(12) United States Patent
Ito et al.

(10) Patent No.: US 7,248,669 B2
(45) Date of Patent: Jul. 24, 2007

(54) METHOD FOR ANALYZING MEMBRANE STRUCTURE AND APPARATUS THEREFOR

(75) Inventors: Yoshiyasu Ito, Ome (JP); Kazuhiko Omote, Akiruno (JP)

(73) Assignee: Rigaku Corporation, Tokyo (JP)

( * ) Notice: Subject to any disclaimer, the term of this patent is extended or adjusted under 35 U.S.C. 154(b) by 228 days.

(21) Appl. No.: 10/958,249

(22) Filed: Oct. 6, 2004

(65) Prior Publication Data
US 2005/0102110 A1   May 12, 2005

(30) Foreign Application Priority Data
Oct. 6, 2003   (JP)   ............................. 2003-347224

(51) Int. Cl.
*G01N 23/20* (2006.01)
*G01T 1/36* (2006.01)

(52) U.S. Cl. .......................................... 378/70; 378/83
(58) Field of Classification Search ................. 378/70, 378/83, 98.8
See application file for complete search history.

(56) References Cited

U.S. PATENT DOCUMENTS 6,025,596 A * 2/2000 Shirai et al. ........... 250/339.11
6,907,107 B1 * 6/2005 Wallis et al. ................. 378/83
2002/0150208 A1 * 10/2002 Yokhin et al. ............... 378/82

FOREIGN PATENT DOCUMENTS

JP   9-105726   4/1997

* cited by examiner

*Primary Examiner*—Edward J. Glick
*Assistant Examiner*—Irakli Kiknazde
(74) *Attorney, Agent, or Firm*—Wenderoth, Lind & Ponack, L.L.P.

(57) ABSTRACT

A method and apparatus for analyzing a membrane structure by fitting simulated operation data to measured data obtained by X-ray reflectivity measurement to analyze the membrane structure. The analysis result obtained by the fitting can be prevented from falling into a local solution, so as to obtain an analysis result of the membrane structure with high accuracy. The method for analyzing a membrane structure for analyzing a structure of a membrane specimen having a single layer membrane or a multi-layer membrane by an X-ray reflectivity measurement, includes a step of simultaneously analyzing plural pieces of measured data obtained by measuring the membrane specimen under plural sets of measuring conditions different from each other in at least one of a resolution and a dynamic range.

10 Claims, 6 Drawing Sheets

METHOD FOR ANALYZING MEMBRANE STRUCTURE AND APPARATUS THEREFOR

BACKGROUND OF THE INVENTION

1. Field of the Invention

The present invention relates to a method for analyzing a membrane structure and an apparatus therefor. More particularly, the invention relates to a method for analyzing a membrane structure by simultaneously fitting simulated operation data to measured data obtained with an optical system utilizing at least two sets of resolutions and dynamic ranges, and an apparatus therefor.

2. Description of the Related Art

In the X-ray reflectivity measurement, an interference phenomenon of X-rays reflected on interfaces among layers of a membrane is measured, and simulated operation data is fitted to the measurement results to analyze density, membrane thickness and roughness of the respective layers. The density of the outermost thin layer can be calculated from the total reflection critical angle, and the densities of the other layers can be calculated from the amplitudes of the interference fringes. The membrane thickness of the layers can be calculated from the frequencies of vibrations. The roughness can be calculated from the attenuation ratio of the total reflectivity measurement data and the attenuation of the amplitudes of the interference fringes on the higher angle side (as described for example in JP-A-2001-349849).

In the case where the X-ray reflectivity measurement is applied to a multi-layer thin membrane having a layer thickness of several hundred nanometers, it is necessary that the measurement is carried out with the divergence angle and the wavelength spread of the incident X-ray being set to sufficiently small values. For example, a perfect crystal monochromator of Si or Ge is used on the incident side. The perfect crystal monochromator suppresses the wavelength of the X-ray generated by a light source from being spread and abstracts only the parallel component from the X-ray, and therefore, the intensity of the X-ray thus irradiating the thin membrane is reduced by about from 1/10 to 1/100 in comparison to the case using no perfect crystal monochromator. In the case where a four-crystal optical system is used, in particular, the intensity of the incident X-ray is reduced to about 1/100, and there are some cases where a sufficient dynamic range cannot be obtained upon X-ray reflectivity measurement.

That is, in the case where the perfect crystal monochromator is used, the measurement cannot be attained to the higher angle side due to the small dynamic range, and there are some cases where the roughness cannot be sufficiently evaluated. In the case where a thin layer is present in the multi-layer membrane, furthermore, there are some cases where the fitting goes with neglecting the layer since the period of vibration corresponding to the layer thickness is small.

FIG. 3 shows a profile as a result of analysis of measurement data of an Si thin membrane with an optical system using a Ge(220) four-crystal monochromator (divergence angle of incident X-ray: about 0.0045°). As a result of fitting of simulated data to the measured data, it is expected that the thin membrane is a single layer membrane formed on a substrate, and in the analysis results shown in Table 2 below, the R value is 0.01586, which shows good agreement.

TABLE 2

| | Density (g/cm³) | Thickness (nm) | Roughness (nm) | R value |
|---|---|---|---|---|
| Si₂O₃CH₃ | 1.012 | 398.30 | 1.45 | 0.01586 |
| Si substrate | 2.33 | — | 0.81 | |

However, in the case where the fitting is again carried out with different initial values set to the parameters including density, thickness and roughness of the membrane, the fitting results in the profile shown in FIG. 4, which converges to a solution shown in Table 3 as different from that shown in Table 2, and the R value of 0.015712 seems to be slightly improved in accuracy.

TABLE 3

| | Density (g/cm³) | Thickness (nm) | Roughness (nm) | R value |
|---|---|---|---|---|
| Si₂O₃CH₃ | 1.012 | 398.30 | 0.44 | 0.015712 |
| Si substrate | 2.33 | — | 1.65 | |

It is understood from the comparison between the results shown in Table 2 and the results shown in Table 3 that the magnitude relation of the interface roughness is reversed.

Such a case that plural solutions are present is often encountered, and it is difficult to evaluate as to which is the correct solution or as to whether both are ascribed to insufficient analysis only by using the measurement results shown in FIGS. 3 and 4. The phenomenon where the roughness values are reversed can be evaluated by measuring data to the higher angle region, but it is impossible to attain sufficient analysis in the case where the dynamic range is short.

SUMMARY OF THE INVENTION

The invention has been made under the aforementioned circumstances, and an object thereof is to provide a method for analyzing a membrane structure by fitting simulated operation data to measured data obtained by X-ray reflectivity measurement to analyze the membrane structure. The analysis result obtained by the fitting can be prevented from falling into a local solution, so as to obtain an analysis result of the membrane structure with high accuracy, and to provide an apparatus therefor.

The invention relates to, as a first aspect, a method for analyzing a membrane structure for analyzing a structure of a membrane specimen having a single layer membrane or a multi-layer membrane by an X-ray reflectivity measurement. The method containing a step of determining the membrane structure by simultaneously analyzing a plurality of pieces of measured data obtained by measuring the membrane specimen under a plurality of sets of measuring conditions which are different from each other in at least one of a resolution and a dynamic range.

The invention also relates to, as a second aspect, a method for analyzing a structure of a membrane containing of the following steps. Fitting simulated operation data obtained through simulation operation carried out by differentiating at least one parameter showing a physical property of a membrane specimen having a single layer membrane or a multi-layer membrane, to measured data obtained with an X-ray incident on the specimen at an angle in a vicinity of a critical angle with respect to a surface of the specimen. Obtaining, as optimum values, values of parameters providing a minimum difference between the measured data and the simulated operation data, so as to determine the structure of the membrane specimen, the simulated operation data being fitted simultaneously to first measured data obtained by irradiating the membrane specimen with an X-ray having a high resolution and second measured data obtained by irradiating the membrane specimen with an X-ray having a low resolution.

The invention further relates to, as a third aspect, an apparatus for analyzing a membrane structure for analyzing a structure of a membrane specimen having a single layer membrane or a multi-layer membrane by an X-ray reflectivity measurement, the apparatus containing the following. A means for measuring a plurality of pieces of data by measuring the membrane specimen under a plurality of sets of measuring conditions different from each other in at least one of a resolution and a dynamic range. A means for simultaneously analyzing the plurality of pieces of data measured by the measuring means, so as to determine the structure of the membrane specimen.

The invention further relates to, as a fourth aspect, an apparatus for analyzing a structure of a membrane containing the following. A means for fitting simulated operation data obtained through simulation operation carried out by differentiating at least one parameter showing a physical property of a membrane specimen having a single layer membrane or a multi-layer membrane, to measured data obtained with an X-ray incident on the specimen at an angle in a vicinity of a critical angle with respect to a surface of the specimen. A means for obtaining, as optimum values, values of parameters providing a minimum difference between the measured data and the simulated operation data, so as to determine a structure of the membrane specimen, the simulated operation data being fitted simultaneously to first measured data obtained by irradiating the membrane specimen with an X-ray having a high resolution and second measured data obtained by irradiating the membrane specimen with an X-ray having a low resolution.

According to the method for analyzing a membrane structure and the apparatus of the invention, the simulated operation data is fitted to the measured data obtained by X-ray reflectivity measurement to analyze the membrane structure, in which the analysis result obtained by the fitting can be prevented from falling into a local solution, so as to obtain an analysis result of the membrane structure with high accuracy.

DESCRIPTION OF THE PREFERRED EMBODIMENTS

Figure 1:
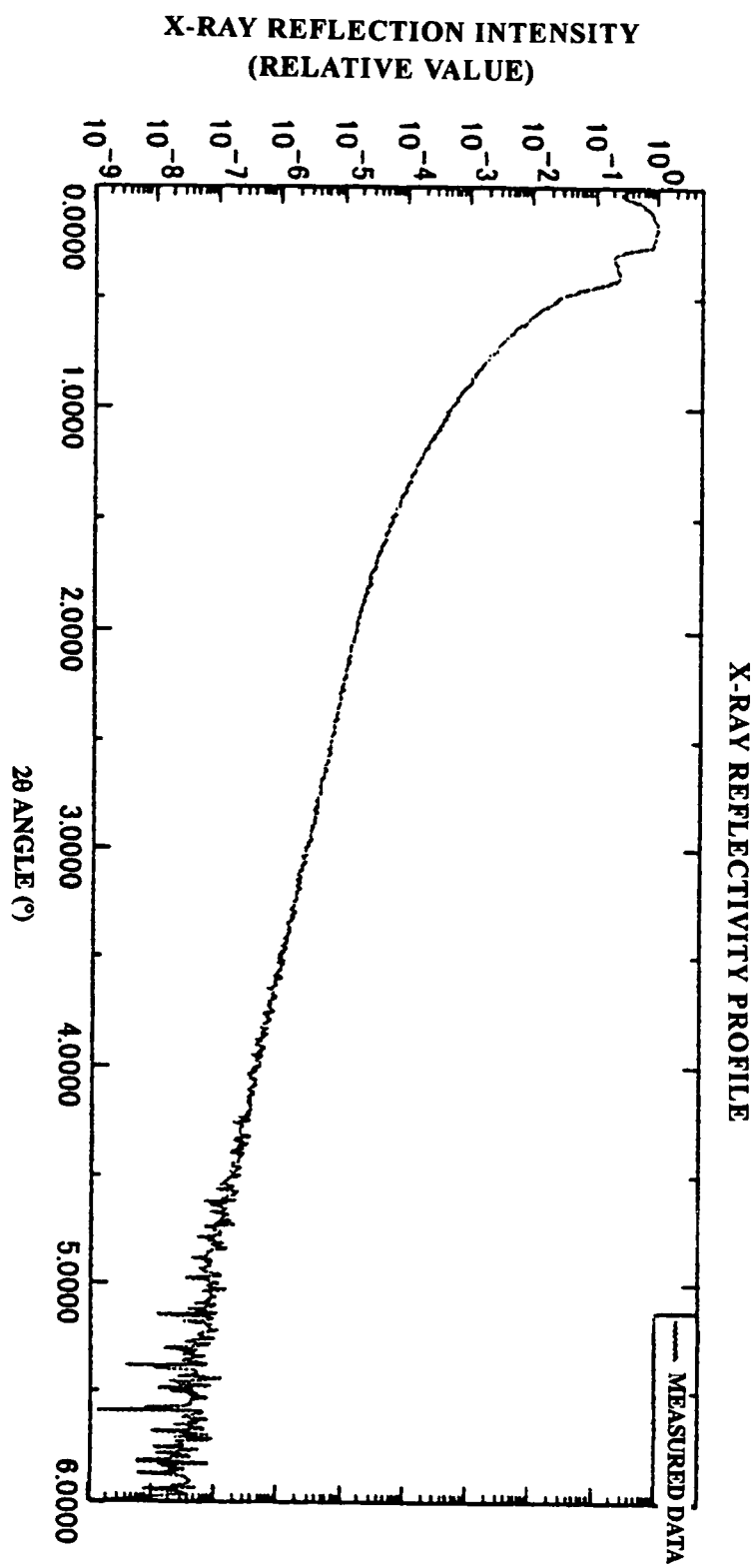
FIG. 1 is a graph showing an example of measured data obtained in the method for analyzing a membrane structure according to the invention.

The method for analyzing a membrane structure according to the invention is a method for analyzing a membrane structure for analyzing a structure of a membrane specimen having a single layer membrane or a multi-layer membrane by an X-ray reflectivity measurement, and a plurality of pieces of measured data, which are obtained by measuring the membrane specimen under a plurality of sets of measuring conditions which are different from each other in at least one of a resolution and a dynamic range, are simultaneously analyzed. Specifically, simulated operation data, which is obtained through simulation operation carried out by differentiating at least one parameter showing a physical property of a membrane specimen having a single layer membrane or a multi-layer membrane, is fitted to measured data, which is obtained with an X-ray incident on the specimen at an angle in a vicinity of a critical angle with respect to a surface of the specimen, so as to determine the structure of the membrane specimen.

As a procedure for the fitting, for example, analysis by the method of least squares may be employed, in which an X-ray reflectivity is calculated according to a parameter, which is a factor for obtaining the reflectivity, being incrementally adjusted, for minimizing the residual sum of squares to the actual reflectivity data. Accordingly, one set of parameters that is most fitting to the measured data can be obtained.

In the analysis by the method of least squares, a problem arises because the residual sum of squares is simply minimized based on the order and method of fitting or adequacy and inadequacy of the initial value. Accordingly, the fitting often fails to complete due to divergence. It has been known that in the ordinary analysis, the solution is converged by carrying out the fitting of simulated operation data to measured data of X-ray reflectivity in the following order.

1. A layer structure model of thin layers including a substrate is formed.

2. With respect to the measured data and the simulated operation data, the maximum intensities are conformed at an angle lower than the critical angle.

3. The background intensity of the model is conformed to the intensity of the measured data.

4. A parameter to be fixed is selected from the parameters of the model. In many cases, the substrate is known, and therefore, the density thereof is fixed. In the case where other parameters, such as thickness and density, are known, they are determined as constants.

5. The parameters are manually determined in such a manner that the measured data is visually conformed to the simulated operation data.

6. Automatic fitting is carried out.

7. A value of the parameter providing a minimum difference between the measured data and the simulated operation data is obtained as an optimum value. At this time, the residual of the minimum sum of squares is in the second decimal place or less (in an order of $10^{-2}$ or less), it is determined that the fitting is completed with substantial accuracy.

In the method for analyzing a membrane structure according to the invention, upon measurement, the simulated operation data is fitted simultaneously to the first measured data obtained by irradiating the membrane specimen with an X-ray having a high resolution and the second measured data obtained by irradiating the membrane specimen with an X-ray having a low resolution, so as to optimize the parameters.

For example, the first measured data is obtained by making an X-ray incident on the membrane specimen through a perfect crystal monochromator, and the second measured data is obtained by making an X-ray incident on the membrane specimen through no perfect crystal monochromator. The simulated operation data is then fitted simultaneously to both the first and second measured data, so as to optimize the parameters. In the case where the measurement is carried out with a perfect crystal monochromator provided on the incident side, measured data with a high resolution and a narrow dynamic range is obtained, and in the case where the measurement is carried out with no perfect crystal monochromator provided on the incident side, measured data with a low resolution and a broad dynamic range is obtained.

FIG. 1 is a result of measurement carried out with no perfect crystal monochromator provided on the incident side (divergence angle: 0.05°, dynamic range: 9 digits). It is understood that a broad dynamic range is obtained, and vibrations with a large period are observed. It is expected from the result that the thin membrane as the specimen has an extremely thin layer. However, a vibration corresponding to a layer having a thickness of about 400 nm cannot be observed in the measurement because of the low resolution optical system.

Figure 2:
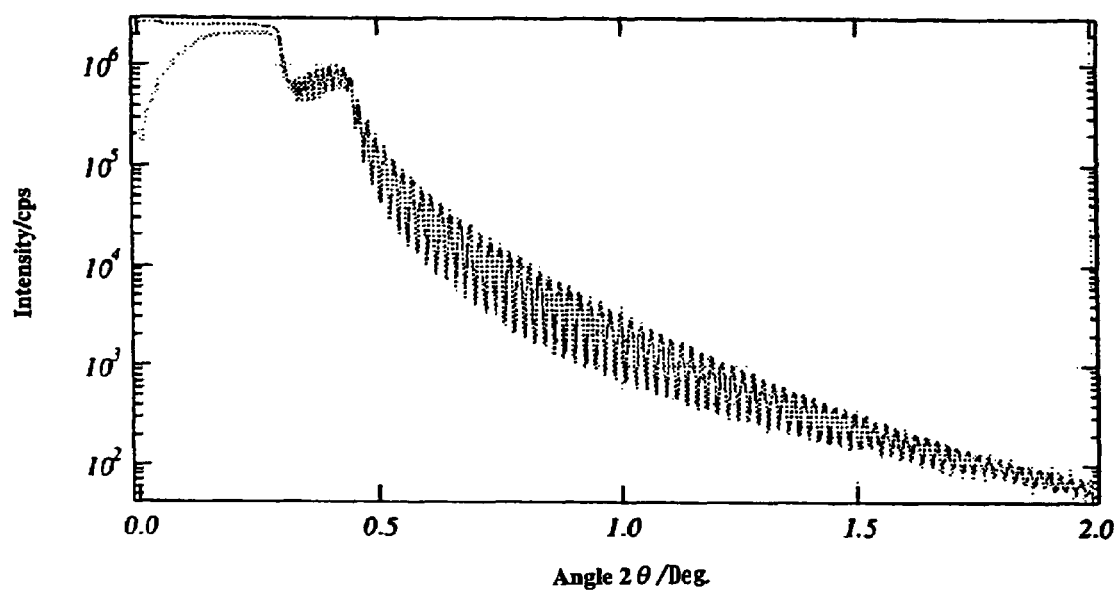
FIG. 2 is a graph showing a result of optimization by fitting carried out in the method for analyzing a membrane structure according to the invention.
Figure 2:
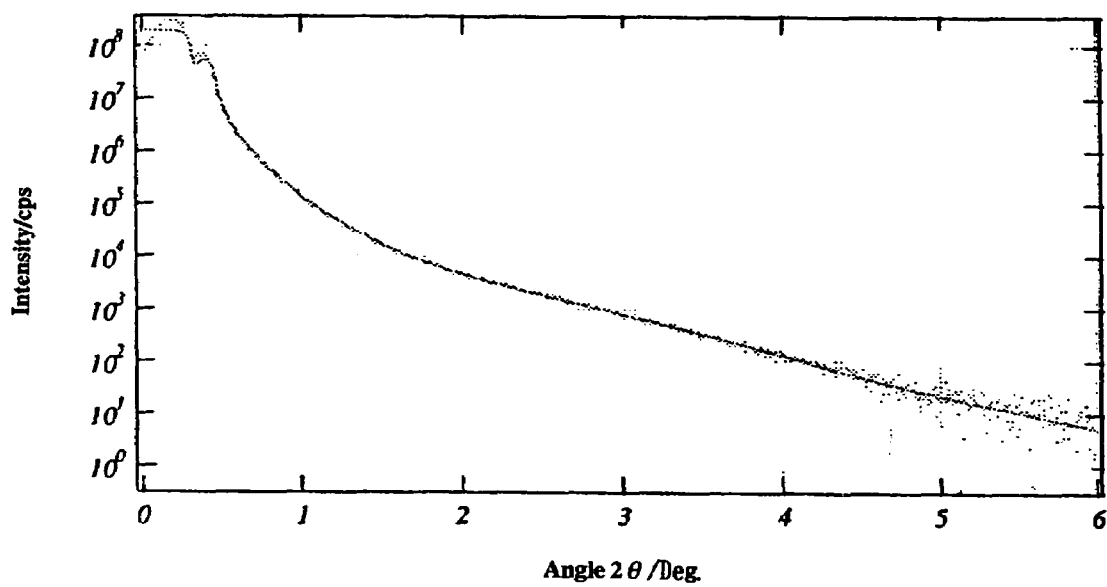
Figure 3:
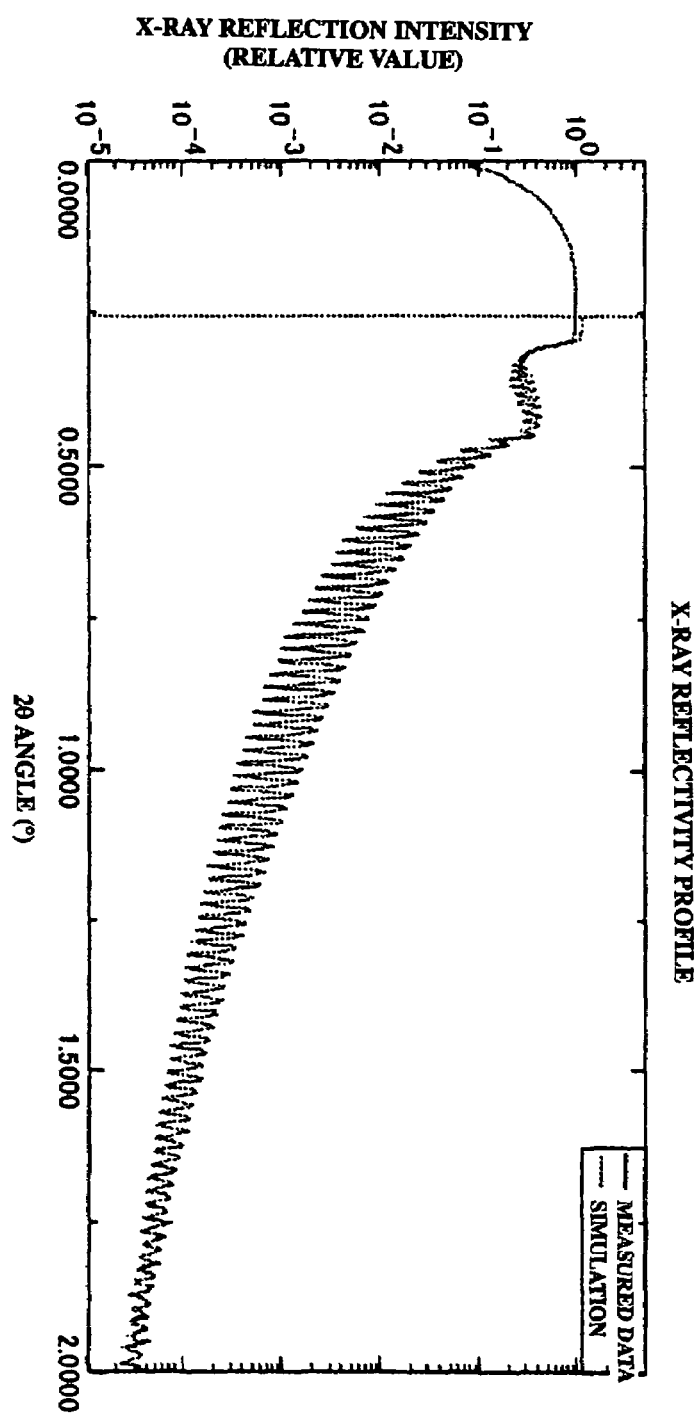
FIG. 3 is a graph showing a result of optimization by fitting carried out in the conventional method for analyzing a membrane structure.
Figure 4:
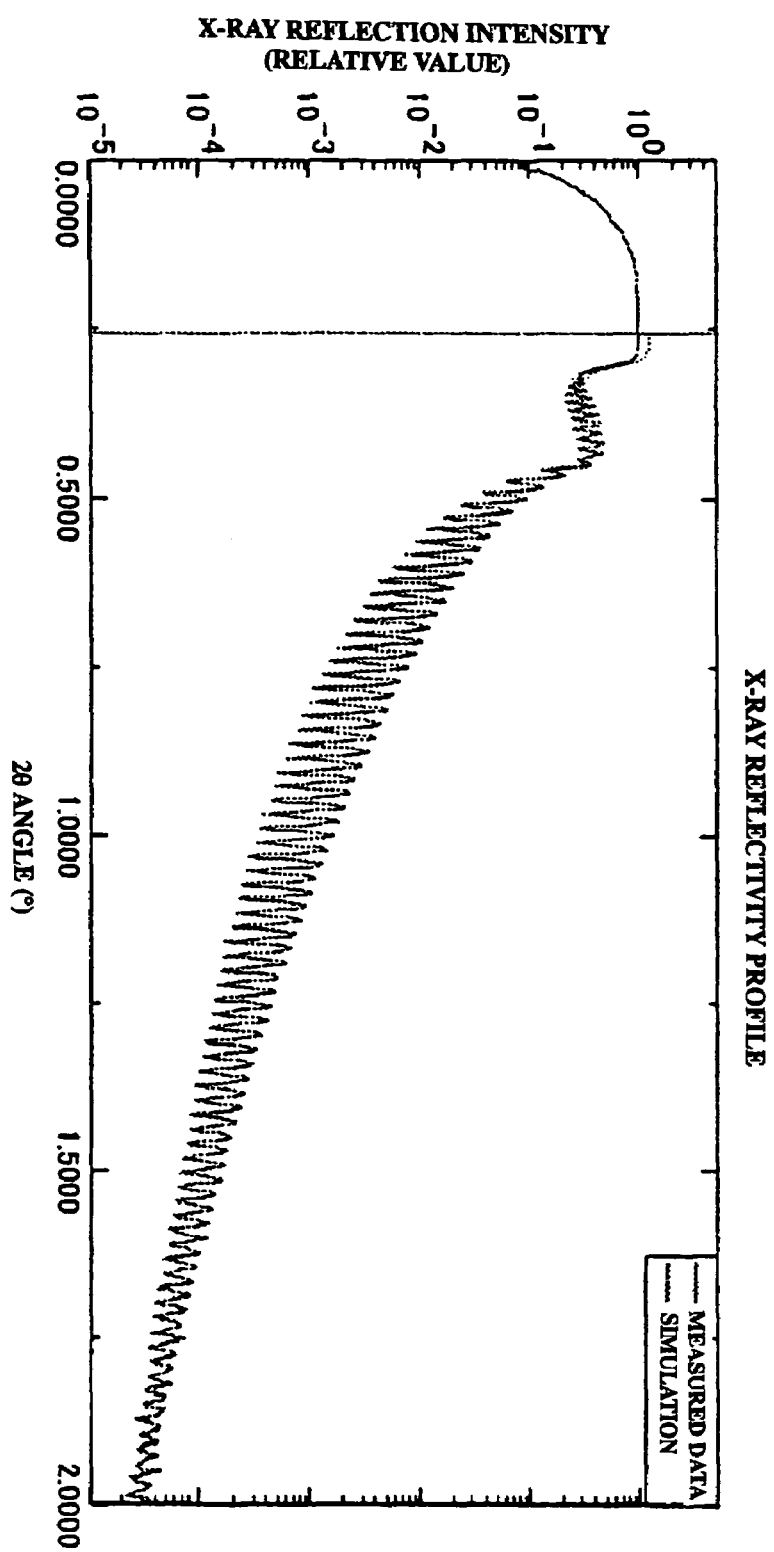
FIG. 4 is a graph showing a result of optimization by fitting carried out in the conventional method for analyzing a membrane structure.
Figure 5A:
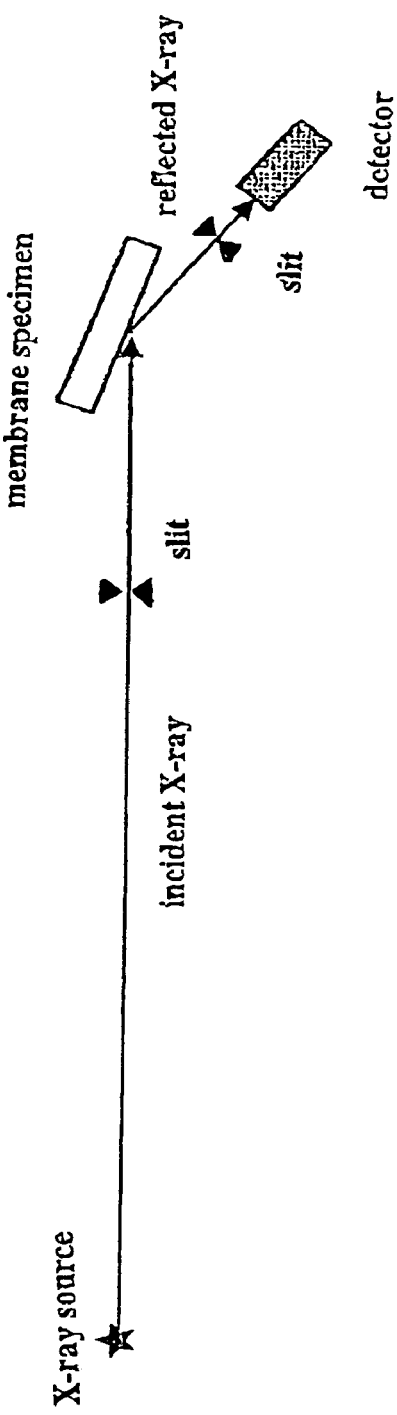
FIG. 5a is a schematic diagram of the X-ray reflectivity measuring device in which no perfect crystal monochromator is provided.
Figure 5B:
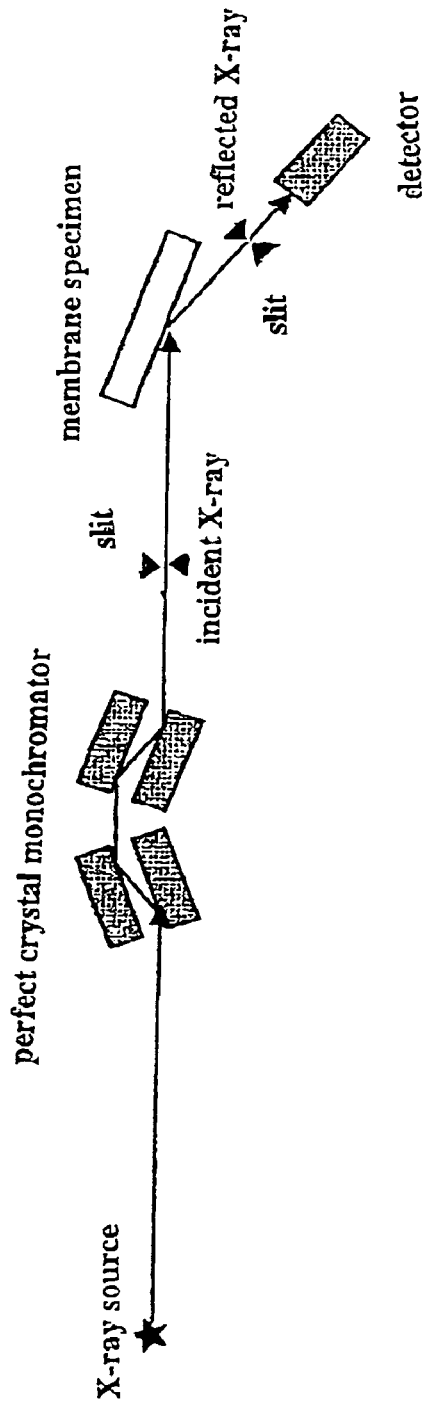
FIG. 5b is a schematic diagram of the X-ray reflectivity measuring device in which a perfect crystal monochromator is provided.
Figure 6:
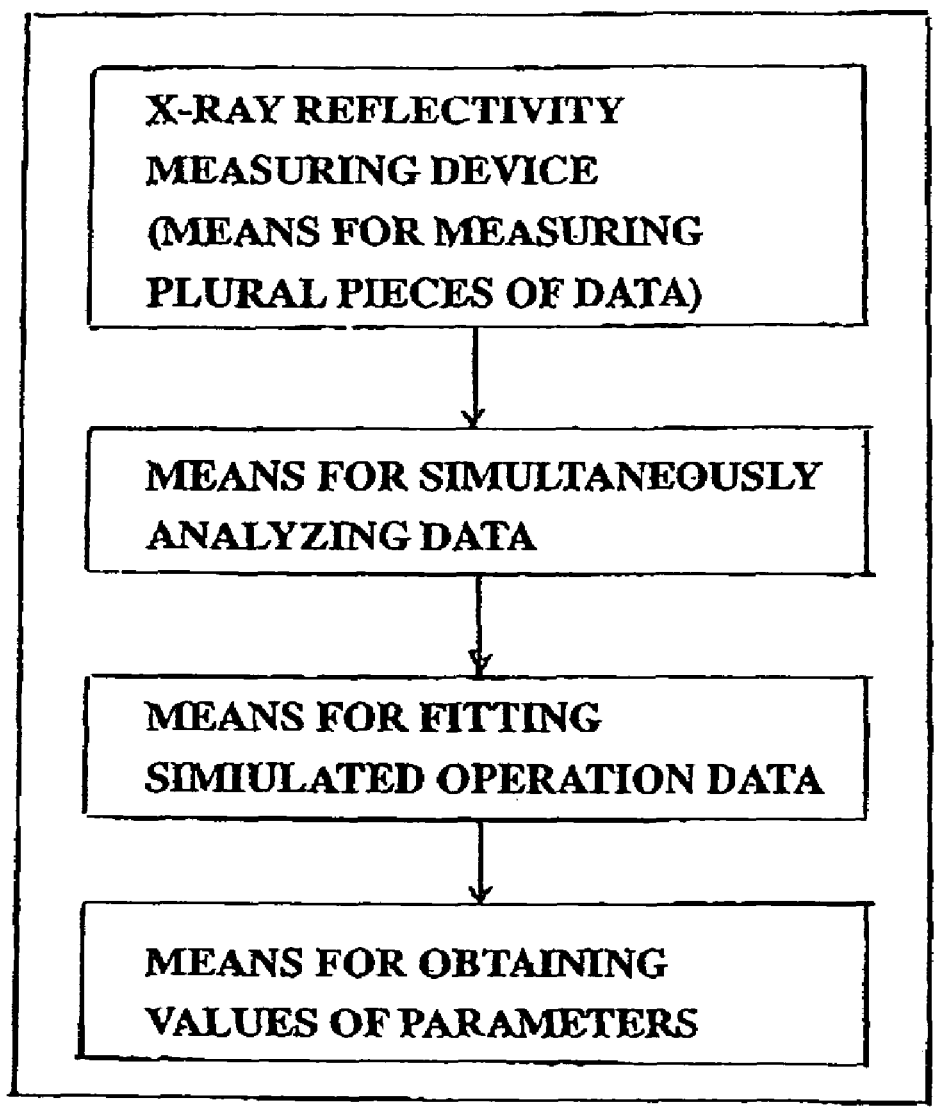
FIG. 6 is a block diagram of a membrane structure analyzer for analyzing a membrane structure.

FIG. 2 is the simulation measured data obtained as a result of simultaneous fitting to the first measured data and the second measured data. The optimum parameters showing the structure of the membrane specimen obtained as results of fitting are shown in Table 1.

TABLE 1

|  | Density (g/cm$^3$) | Thickness (nm) | Roughness (nm) | R value |
|---|---|---|---|---|
| Si$_2$O$_3$CH$_3$ | 1.012 | 398.47 | 1.63 | 0.027637 |
| SiO$_2$ | 2.25 | 2.83 | 0.40 |  |
| Si substrate | 2.33 | — | 0.42 |  |

It is understood from the aforementioned analysis that an SiO$_2$ oxide layer is formed, which has not appeared in the case where the fitting is carried out by using only the measured data obtained with a perfect crystal monochromator provided on the incident side. Furthermore, the accurate solution is obtained for the roughness without falling into a local solution.

As having been described, the roughness and the thickness of the membrane can be simultaneously analyzed by fitting two pieces of data with conditions different from each other in resolution and dynamic range. The number of pieces of data with conditions different from each other in resolution and dynamic range may be two or more. The similar effect as differentiating the resolution and the dynamic range can be expected, for example, by selecting plural wavelengths for simultaneous analysis of data.

The apparatus for analyzing a membrane structure according to the invention has a constitution for practicing the aforementioned method for analyzing a membrane structure. Specifically, the apparatus for analyzing a membrane structure according to the invention has, as a basic constitution, an X-ray reflectivity measuring device for practicing X-ray reflectivity measurement, and contains a means for measuring a plurality of pieces of data by measuring one membrane specimen under a plurality of sets of measuring conditions different from each other in at least one of a resolution and a dynamic range, and a means for simultaneously analyzing the plurality of pieces of data measured by the measuring means, so as to determine a structure of the membrane specimen.

More specifically, the apparatus for analyzing a membrane structure according to the invention may have such a constitution that contains an ordinary apparatus for measuring X-ray reflectivity equipped, in which a perfect crystal monochromator is movably provided on the X-ray incident side. Upon measurement, an X-ray is incident on a membrane specimen through the perfect crystal monochromator to obtain the first measured data, and then after moving the perfect crystal monochromator, an X-ray is incident on a membrane specimen through no perfect crystal monochromator to obtain the second measured data. The first measured data and the second measured data thus obtained are loaded to the means for determining the membrane structure, such as a computer, and subjected to the method for analyzing a membrane structure having been described in detail, so as to calculate optimum parameters showing the membrane structure.

The invention has been described with reference to the aforementioned examples, but the invention is not construed as being limited to them, and various changes and modifications in detail may be made therein without departing from the spirit and scope thereof.

According to the invention, in the method for analyzing a membrane structure by fitting simulated operation data to measured data obtained by X-ray reflectivity measurement to analyze the membrane structure, the analysis result obtained by the fitting can be prevented from falling into a local solution, so as to obtain an analysis result of the membrane structure with high accuracy.

There are some cases in the conventional techniques that the dynamic range is narrowed as a result of improvement in resolution to fail to obtain information sufficient for analyzing a membrane structure, and the parameters used in fitting are converged to a local solution. In the invention, measured data with a high resolution and a narrow dynamic range and measured data with a low resolution and a broad dynamic range are used to enable fitting to such data that reflects the overall structure of the membrane specimen, whereby the aforementioned problem of local solution is resolved. In other words, according to the invention, parameters showing a structure can be obtained with high accuracy even in the case of a membrane specimen having a complex layer structure.

The X-ray reflectivity measurement is being widely used for evaluation of functions and characteristics of various functional thin membrane materials, and it is considered that the method for analyzing a membrane structure and the apparatus therefor according to the invention realizing structure analysis with high accuracy are considerably useful, and practical applications thereof are strongly expected.

What is claimed is:

1. A method for analyzing a membrane structure of a single layer or multi-layer membrane specimen according to an X-ray reflectivity measurement conducted using a specified range of angles of X-ray reflection with respect to a surface of the membrane specimen, said method for analyzing a membrane structure comprising:

measuring the X-ray reflectivity of the membrane specimen using a plurality of different measuring conditions, including a measuring condition with a high resolution and a narrow dynamic range when the angle of X-ray reflection is on a high side of the specified range of angles and including a measuring condition with a low resolution and a wide dynamic range when the angle of X-ray reflection is on a low side of the specified range of angles;

generating a plurality of sets of measured data based on said measuring of the X-ray reflectivity;

generating a plurality of reflectivity curves according to the plurality of sets of measured data;

simultaneously analyzing the plurality of reflectivity curves to determine the membrane structure;

and providing an output signal indicative of the membrane structure.

2. The method for analyzing a membrane structure according to claim 1, wherein the specified range of angles includes angles ranging from 0-6 degrees with respect to the surface of the membrane specimen.

3. The method for analyzing a membrane structure according to claim 2, wherein the high side of the specified range of angles includes angles greater than or equal to 3 degrees.

4. The method for analyzing a membrane structure according to claim 2, wherein the low side of the specified range of angles includes angles less than or equal to 3 degrees.

5. A method for analyzing a structure of a membrane specimen comprising:

fitting simulated operation data, obtained by differentiating at least one parameter representing a physical property of the membrane specimen having a single layer or a multi-layer membrane, to measured data obtained according to an X-ray incident on the membrane specimen at an angle in a vicinity of a critical angle with respect to a surface of the membrane specimen;

obtaining optimum values according to values of parameters which provide a minimum difference between the measured data and the simulated operation data;

determining the structure of the membrane specimen according to the optimum values from said obtaining of the optimum values, wherein said fitting of the simulated operation data includes simultaneously fitting the simulated operation data to a first measured data obtained by irradiating the membrane specimen with an X-ray having a high resolution, and fitting the simulated operation data to a second measured data obtained by irradiating the membrane specimen with an X-ray having a low resolution.

6. A membrane structure analyzer for analyzing a membrane structure of a single layer or multi-layer membrane specimen according to an X-ray reflectivity measurement conducted using a specified range of angles of X-ray reflection with respect to a surface of the membrane specimen, said membrane structure analyzer comprising:

a means for measuring the X-ray reflectivity of the membrane specimen using a plurality of different measuring conditions, including a measuring condition with a high resolution and a narrow dynamic range when the angle of X-ray reflection is on a high side of the specified range of angles and including a measuring condition with a low resolution and a wide dynamic range when the angle of X-ray reflection is on a low side of the specified range of angles;

a means for generating a plurality of sets of measured data based on the measuring of the X-ray reflectivity;

a means for generating a plurality of reflectivity curves according to the plurality of sets of measured data; and a means for simultaneously analyzing the plurality of reflectivity curves and for determining the structure of the membrane specimen according to the simultaneous analysis.

7. The membrane structure analyzer according to claim 6, wherein the specified range of angles includes angles ranging from 0-6 degrees with respect to the surface of the membrane specimen.

8. The membrane structure analyzer according to claim 7, wherein the high side of the specified range of angles includes angles greater than or equal to 3 degrees.

9. The membrane structure analyzer according to claim 7, wherein the low side of the specified range of angles includes angles less than or equal to 3 degrees.

10. A membrane structure analyzer for analyzing a structure of a membrane specimen, said membrane structure analyzer comprising:

a means for fitting simulated operation data, obtained by differentiating at least one parameter representing a physical property of the membrane specimen having a single layer or a multi-layer membrane, to measured data obtained according to an X-ray incident on the membrane specimen at an angle in a vicinity of a critical angle with respect to a surface of the membrane specimen;

a means for obtaining optimum values according to values of parameters which provide a minimum difference between the measured data and the simulated operation data;

a means for determining the structure of the membrane specimen according to the optimum values from said means for obtaining the optimum values, wherein, said means for fitting the simulated operation data is operable to simultaneously fit the simulated operation data to a first measured data obtained by irradiating the membrane specimen with an X-ray having a high resolution, and operable to simultaneously fit the simulated operation data to a second measured data obtained by irradiating the membrane specimen with an X-ray having a low resolution.

* * * * *